(12) United States Patent
Chikamune (10) Patent No.: US 9,046,502 B2
(45) Date of Patent: Jun. 2, 2015

(54) LIQUID QUALITY CHECKING DEVICE AND LIQUID STORAGE TANK PROVIDED WITH THE DEVICE

(75) Inventor: Takashi Chikamune, Mito (JP)

(73) Assignee: HITACHI CONSTRUCTION MACHINERY CO., LTD., Tokyo (JP)

( * ) Notice: Subject to any disclaimer, the term of this patent is extended or adjusted under 35 U.S.C. 154(b) by 78 days.

(21) Appl. No.: 13/984,993

(22) PCT Filed: Feb. 6, 2012

(86) PCT No.: PCT/JP2012/052630
§ 371 (c)(1),
(2), (4) Date: Aug. 12, 2013

(87) PCT Pub. No.: WO2012/111469
PCT Pub. Date: Aug. 23, 2012

(65) Prior Publication Data
US 2013/0312497 A1    Nov. 28, 2013

(30) Foreign Application Priority Data
Feb. 18, 2011    (JP) ................. 2011-033088

(51) Int. Cl.
*G01N 33/487*    (2006.01)
*G01N 33/00*    (2006.01)
*G01N 21/29*    (2006.01)
*G01N 21/78*    (2006.01)
*G01N 33/28*    (2006.01)
*G01J 3/52*    (2006.01)

(52) U.S. Cl.
CPC .............. *G01N 33/00* (2013.01); *G01N 21/293* (2013.01); *G01N 21/78* (2013.01); *G01N 33/28* (2013.01); *G01J 3/52* (2013.01)

(58) Field of Classification Search
USPC ............................................... 73/53.01, 54.17
See application file for complete search history.

(56) References Cited

U.S. PATENT DOCUMENTS

| 1,537,519 | A | * | 5/1925 | Yablick ....................... 422/119 |
| 3,585,963 | A | * | 6/1971 | Hiszpanski .................. 116/206 |
| 4,894,342 | A | * | 1/1990 | Guinn et al. ................ 435/297.4 |
| 5,417,204 | A | * | 5/1995 | Moesle, Jr. ................. 128/205.23 |
| 6,197,255 | B1 | * | 3/2001 | Miyake et al. ................. 422/64 |
| 6,937,339 | B2 | * | 8/2005 | Yamazaki et al. ............ 356/427 |

(Continued)

FOREIGN PATENT DOCUMENTS

| CN | 2344309 Y | 10/1999 |
| CN | 2852115 Y | 12/2006 |

(Continued)

*Primary Examiner* — Laura Martin
*Assistant Examiner* — Samir M Shah
(74) *Attorney, Agent, or Firm* — Volpe and Koenig, P.C.

(57) ABSTRACT

A deterioration checking device (2) includes a sight glass (3) through which deterioration of a biofuel stored in a fuel tank is observable as a change in the color of the biofuel, and first and second benchmark sections (4a, 4b) each of which three color samples (11a, 11b, 11c) corresponding to different degrees of deterioration of the biofuel are arranged along the sight glass (3). Deterioration is determined by observing the color samples (11a, 11b, 11c) through the biofuel in the sight glass (3). The arrangement of the color samples (11a, 11b, 11c) of the first benchmark section (4a) and that of the color samples (11a, 11b and 11c) of the second benchmark section (4b) are reversed to each other, so as to cope with the lowering of the liquid level of the biofuel and the rising of the liquid level of a water layer.

6 Claims, 10 Drawing Sheets

(56) References Cited

U.S. PATENT DOCUMENTS

| | | |
|---|---|---|
| 2002/0108639 A1* | 8/2002 | Eiermann et al. ............... 134/18 |
| 2003/0010396 A1* | 1/2003 | Jursich et al. .................. 141/94 |
| 2003/0060984 A1* | 3/2003 | Takezawa et al. .............. 702/28 |
| 2004/0115818 A1* | 6/2004 | Puri et al. ........................ 436/3 |
| 2004/0135089 A1* | 7/2004 | Manz et al. .................. 250/343 |
| 2005/0042136 A1* | 2/2005 | Marganski et al. ............. 422/58 |
| 2007/0129650 A1* | 6/2007 | Freeman et al. .............. 600/583 |
| 2008/0227216 A1 | 9/2008 | Albeck |
| 2009/0048536 A1* | 2/2009 | Freeman et al. .............. 600/583 |
| 2010/0007874 A1* | 1/2010 | Lunati et al. .................... 356/70 |
| 2012/0273697 A1* | 11/2012 | She et al. .................. 250/461.1 |

FOREIGN PATENT DOCUMENTS

| | | | |
|---|---|---|---|
| CN | 200965519 Y | 10/2007 | |
| CN | 101952711 A | 1/2011 | |
| JP | 2008-261812 A | 10/2008 | |
| JP | 2009-235967 A | 10/2009 | |
| JP | 2010-501843 A | 1/2010 | |
| JP | 4483922 B2 | 4/2010 | |
| JP | 2012098235 A * | 5/2012 | ............. G01N 21/78 |

* cited by examiner

LIQUID QUALITY CHECKING DEVICE AND LIQUID STORAGE TANK PROVIDED WITH THE DEVICE

TECHNICAL FIELD

The present invention relates to a liquid quality checking device that is suitable as a device for determining the quality of a liquid, for example, the deterioration of fuel, lubrication oil, hydraulic oil and the like, and a liquid storage tank provided with the device.

BACKGROUND ART

Fuel, lubrication oil, hydraulic oil and the like have been widely used in various machines. For example, a construction machine, such as a hydraulic excavator, uses a fuel to work an internal combustion engine for driving a hydraulic pump, a lubrication oil to lubricate the internal combustion engine and the like, and a hydraulic oil to transmit hydraulic pressure from the hydraulic pump for the purpose of running the construction machine and driving its working mechanism. Such fuel, lubrication oil, hydraulic oil and the like are stored in respective tanks. If the construction machine is not operated over a long period, the fuel, stored in the tank and left still without addition of any fresh fuel, is gradually deteriorated. The lubrication oil and the hydraulic oil are apt to deteriorate by not being refilled or renewed for long periods of time. All these three can be deteriorated if added or mixed with an inferior fuel or oil. Such deterioration causes undesired matters like performance degradation of the internal combustion engine and a decline in operation efficiency or durability of the construction machine. Thus, earlier and timely renewal of the fuel and oils is required before the deterioration progresses.

In late years, biofuels, derived from biomass for example, have been increasingly used as alternative fuels for the internal combustion engine. Biofuel is advantageous in that greenhouse gas emission can be reduced but, on the other hand, is disadvantageous in that metal parts of a fuel supply system are corroded as the biofuel is oxidized, and that proper fuel injection control becomes difficult to perform as the viscosity of the biofuel increases due to oxidation. For this reason, taking care of the deterioration of biofuels is of great importance when the biofuels are used as fuels for the internal combustion engine.

Various measures have been suggested to deal with the above problems. Technologies described in Patent Documents 1 and 2 can be cited as examples of a technology to detect a quality deterioration of biofuels. Based upon the phenomenon in which the color shade of a biofuel changes with the progress of oxidation of the biofuel, the technology disclosed in the Patent Document 1 periodically detects the color shade in terms of light transmittance, sequentially calculates the amount of change with respect to a previous value, and determines a degree of deterioration of the biofuel on the basis of an integrated value obtained by accumulating absolute values of the amounts of change.

According to the technology disclosed in the Patent Document 2, based upon the phenomenon in which the oxygen concentration of a biofuel increases and delay in ignition shortens as the oxidation of the biofuel progresses, an ignition delay derived on the basis of the in-cylinder pressure during operation of the internal combustion engine. If the derived ignition delay is shorter than a reference value by a predetermined amount or more, it is determined that the biofuel is deteriorated.

PRIOR ART DOCUMENTS

Patent Documents

Patent Document 1: Japanese Patent No. 4483922
Patent Document 2: Unexamined Japanese Patent Publication No. 2009-235967

SUMMARY OF THE INVENTION

Problems to be Solved by the Invention

The technology disclosed in the Patent Document 1 requires a light transmission rate sensor that detects the light transmission rate, and the technology disclosed in the Patent Document 2 requires an in-cylinder pressure sensor that detects the in-cylinder pressure. Further, both of these technologies require a processing circuit that determines the degree of deterioration of the biofuel on the basis of its detected value. The technologies of the Patent Documents 1 and 2 are therefore not only complicated and expensive as an overall system but insufficient in reliability considering failure that might arise out of their complexity.

Needless to say, these conventional technologies could be applied to the determination of deterioration of ordinary fossil fuels, lubrication oils, hydraulic oils and the like. Even in such case, the abovementioned problems still remain unsolved. Especially the construction machine as described above, which simultaneously uses fuel, lubrication oil and hydraulic oil, requires respective devices for determining the deterioration of the fuel and oils. Thus, there has been a demand for simpler and less expensive devices.

The present invention has been made in light of the foregoing problems. It is an object of the invention to provide a liquid quality checking device that accurately determines the quality of liquids, including fuel, lubrication oil, hydraulic oil and the like, with a system configuration that is simple, inexpensive and highly reliable, and a liquid storage tank provided with the device.

Means for Solving the Problems

In order to accomplish the object, the liquid quality checking device of the invention comprises an observation window that is attachable onto a liquid storage tank and extends in a vertical direction in which a liquid level of a liquid stored in the liquid storage tank changes, the observation window permitting a change in quality of the liquid to be observed as a change in color of the liquid, and first and second benchmark sections that are placed close to the observation window and each have a plurality of color samples corresponding to a plurality of different quality degrees of the liquid and arranged along the observation window.

Wherein in the first benchmark section, the color samples are arranged along the observation window in order of specific stages through which deterioration of the liquid quality progresses, and in the second benchmark section, the color samples are arranged along the observation window in order reverse to the order of the color samples of the first benchmark section.

Preferably, in the above liquid quality checking device of the present invention, the color samples are formed by filling transparent capsules with liquids at different quality degrees.

The invention encompasses a liquid storage tank provided with the liquid quality checking device.

Preferably, in the above liquid storage tank of the present invention, a vertical position of the liquid quality checking device is set so that a lower end of the observation window is located above a allowable highest position that a liquid level of a contaminant forming a layer under the liquid in the liquid storage tank can lower.

Advantageous Effects of the Invention

As described above, the liquid quality checking device of the invention has the observation window through which a change in quality of the liquid stored in the liquid storage tank is observable in terms of a change in color of the liquid, and the first and second benchmark sections in each of which the color samples corresponding to the liquid quality degrees are arranged along the observation window, and the color samples of the first and second benchmark sections are reversely arranged.

The quality degree(deterioration degree) of the liquid stored in the liquid storage tank can be determined by making a comparison between the color change of the liquid, which is observable through the observation window, and the color samples of the first and second benchmark sections. In this way, the liquid quality checking can be carried out with a simple and inexpensive system configuration including the observation window and the first and second benchmark sections. The liquid quality checking device is thus unlikely to break down and highly reliable.

The liquid level changes depending upon the liquid storage amount in the liquid storage tank. Similarly, when a contaminant that has entered into the liquid storage tank for some reason forms a layer under the liquid (for example, a water layer formed by dew condensation), the liquid level changes because of the contaminant layer. This causes an area, through which the liquid color change is observable, to be narrowed and shifted to a lower or upper part of the observation window. Because of the reverse arrangement of the color samples of the two benchmark sections, even if the observable area is limited to either the lower or upper part of the observation window, the liquid quality degree can be determined by comparison with the color samples of either one of the benchmark sections. The liquid quality degree can be thus determined under more circumstances than ever before, regardless of a change in the liquid level of the liquid or the contaminant(water) layer.

According to the liquid quality checking device of the present invention, preferably, liquids at different quality stages are filled into the respective transparent capsules to be used as color samples. Since the color samples are actual liquids with the respective different qualities, deterioration degree can be determined with higher accuracy.

According to the liquid storage tank of the present invention, the tank is provided with the liquid quality checking device of the present invention, so that the above-described operation and advantages can be obtained.

According to the liquid storage tank provided with the liquid quality checking device of the present invention, the vertical position of the liquid quality checking device is set so that a lower end of the observation window is located above the allowable highest position that the liquid level of the contaminant which has entered into the liquid storage tank can lower after drainage. A change in the liquid color can therefore be observed through the whole area of the observation window without being obstructed by the contaminant layer, and the liquid quality degree can be accurately determined by comparison with the color samples.

MODE FOR CARRYING OUT THE INVENTION

Embodiments of the present invention will be described below, in which the invention is embodied as a biofuel deterioration checking device (liquid quality checking device) mounted on a hydraulic excavator, and as a fuel tank (liquid storage tank) provided with the device.

Although not shown, the hydraulic excavator utilizes hydraulic pressure produced by a hydraulic pump, which is driven by an internal combustion engine, to travel by itself and to actuate its working mechanism like a excavating bucket.

The internal combustion engine can run by using the biofuel stored in the fuel tank. As mentioned in the Background Art, the biofuel, if deteriorated, causes the problem of corrosion of the fuel supply system of the internal combustion engine and the problem of adverse effects on fuel injection control that arises from oxidation and consequent increased viscosity of the biofuel. To deal with these problems, the fuel tank is provided with the deterioration checking device. The deterioration checking device can be used to determine a deteriorated quality of the biofuel in the fuel tank, and make it possible to promptly and timely refuel or renew the biofuel, when the deteriorated fuel is observed.

The hydraulic excavator uses lubrication oil for lubricating the internal combustion engine and hydraulic oil for hydraulic pressure transmission. To avoid problems associated with the deterioration of these oils, oil tanks storing the lubrication and hydraulic oils are also provided with deterioration excavator devices for determining the deterioration, respectively. Structures of the checking devices for determining the deterioration of these oils are identical or similar to that of the checking device for the biofuel, and therefore, the fuel tank for biofuel provided with the deterioration checking device will be described below as a representative.

Figure 1:
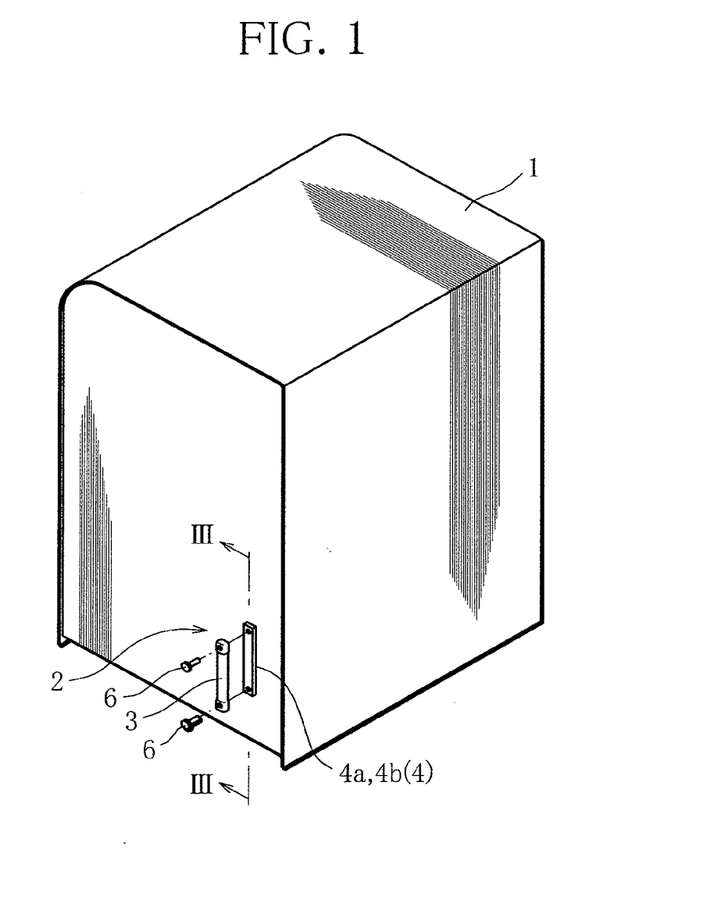
FIG. 1 is a perspective view showing a fuel tank for storing a biofuel according to an embodiment of the present invention.

FIG. 1 is a perspective view showing the fuel tank that stores a biofuel. The fuel tank 1 is made of steel plates and has a rectangular parallelepiped shape. The fuel tank 1 is mounted on an upper swing structure of the hydraulic excavator in the attitude shown in FIG. 1. Although not shown, a fuel filler opening is formed in a lateral side wall of the fuel tank 1, and a fuel pipe extending to the internal combustion engine is connected to a fuel supply port formed in the same lateral side wall of the fuel tank 1. The biofuel is fed into the fuel tank 1 through the fuel filler opening. When the hydraulic excavator is in operation, the biofuel in the fuel tank 1 is supplied to the internal combustion engine through the fuel pipe. A drain port is also formed in the bottom of the fuel tank 1. The drain port is used for drainage of the deteriorated biofuel and/or water produced as a result of dew condensation in the tank.

Figure 2:
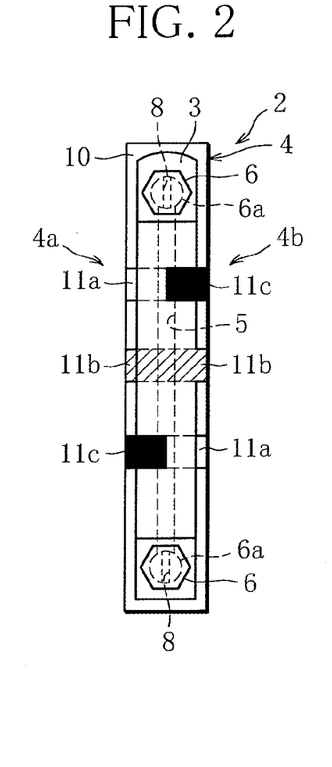
FIG. 2 is an elevation view of a deterioration checking device.
Figure 3:
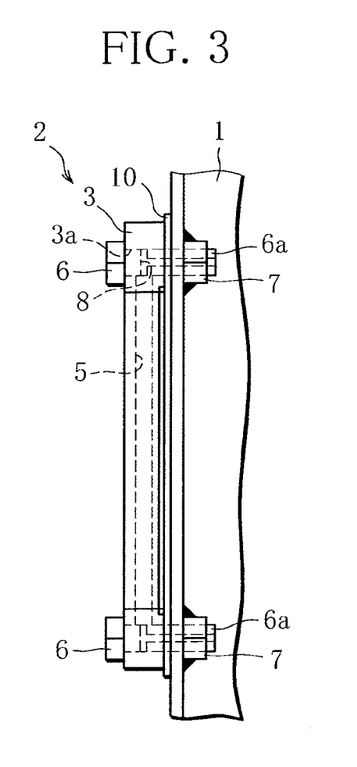
FIG. 3 is a cross-sectional view of the deterioration checking device, taken along the line in FIG. 1.
Figure 4:
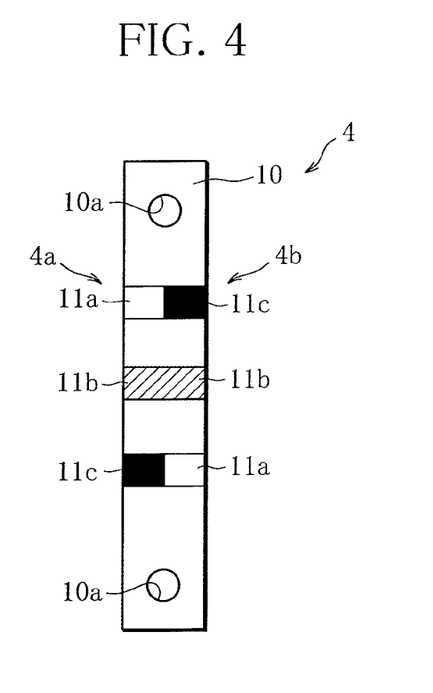
FIG. 4 is an elevation view of a benchmark section of the deterioration checking device.
Figure 5:
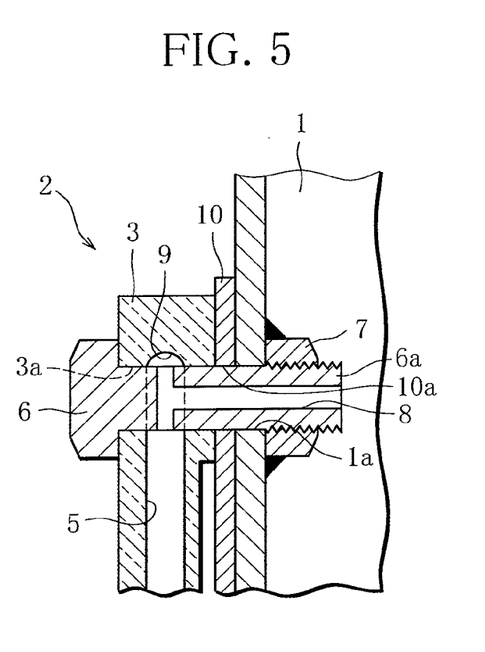
FIG. 5 is an enlarged sectional view of an upper fastened portion of a sight glass.

FIG. 2 is an elevation view of the deterioration checking device. FIG. 3 is a cross-sectional view of the deterioration checking device, taken along the line in FIG. 1. FIG. 4 is an elevation view of a benchmark section of the deterioration checking device. FIG. 5 is an enlarged sectional view of an upper fastened portion of a sight glass. Although not shown in detail, a lower fastened portion of the sight glass is similar to the one shown in FIG. 5.

The biofuel deterioration checking device 2 is placed in a lower corner of an outer side wall of the fuel tank 1. The deterioration checking device 2 includes a sight glass 3 (observing section), into which the biofuel in the fuel tank 1 is introduced, and a benchmark section 4 with color samples for deterioration determination. The sight glass 3 is made of transparent glass or acrylic resin and has a tubular shape extending in a vertical direction, that is, along a direction in which the liquid level of the biofuel changes in the fuel tank 1. The sight glass 3 has an inner passage as a fuel-display passage 5, which extends in the vertical direction.

Two bolt holes 3a for fastening are formed through upper and lower end portions of the sight glass 3, respectively, and directed toward the fuel tank 1. The upper and lower bolt holes 3a communicate with upper and lower ends of the fuel-display passage 5, respectively. Union bolts 6 are inserted through the respective upper and lower bolt holes 3a. The sight glass 3 is fastened to the fuel tank 1 by the union bolts 6 whose shank 6a through respective bolt holes 1a formed through the side wall of the fuel tank 1 and are engaged with respective weld nuts 7 welded to the inner side wall of the fuel tank 1 for fastening.

A T-shaped fuel passage 8 is formed in the shank 6a of each union bolt 6. The T-shaped fuel passage 8 opens into the fuel tank 1 at the tip end of the shank 6a and communicates with the fuel-display passage 5 of the sight glass 3 at the base end of the shank 6a. An annular fuel passage 9 is formed around the entire circumference of the bolt hole 3a, so that the T-shaped fuel passage 8 and the fuel-display passage 5 always communicate with each other through the annular fuel passage 9, regardless of the rotational position of the bolt. Consequently, the fuel-display passage 5 communicates with the fuel tank 1 through the T-shaped fuel passages 8 of the upper and lower union bolts 6, so that the biofuel stored in the tank 1 is introduced into the fuel-display passage 5 as well. Although not shown, the sight glass 3 is liquid-tightly fastened by the union bolts 6 using proper packing to prevent the biofuel from leaking outside.

A base plate 10 of the benchmark section 4 is made of a steel plate and has a rectangular shape extending in the vertical direction. The base plate 10 is securely interposed between the outer side wall of the fuel tank 1 and the sight glass 3 with the shanks 6a of the union bolts 6 inserted through bolt holes 10a, which are formed through the upper and lower end portions of the plate 10. Color samples are printed separately on the right and left sides of the surface of the base plate 10 (the surface facing the sight glass 3). The color samples on the right side and those on the left side function independently as benchmark sections as mentioned later. Hereinafter, a region of the color samples on the left side as viewed in the figures will be referred to as a first benchmark section 4a, and a region of the color samples on the right side as a second benchmark section 4b.

The entire surface of the base plate 10 is printed in white, and a set of three color samples is printed on each of the first and second benchmark sections 4a and 4b. The three color samples of the benchmark sections 4a and 4b are arranged by hues and/or tones corresponding to color changes of the biofuel, which are caused by the deterioration(or aging) of the biofuel. The biofuel originally has a yellow hue for example, and has a property that its brightness gradually decreases with deterioration (or aging), shifting from a light shade to a deep one. To be specific, color of the biofuel changes from pale yellow, which is a color when the biofuel is fresh, to dark brown, which indicates that the biofuel has reached a use limit thereof. The three color samples are, for example, yellow that is the color when the biofuel is almost fresh (hereinafter, referred to as first color 11a), dark brown indicating the use limit (hereinafter, referred to as third color 11c), and ocher that is an intermediate color therebetween (hereinafter, referred to as second color 11b). These color samples 11a, 11b and 11c are printed on the base plate 10.

The biofuel changes in color from the first color 11a to the second color 11b, and to the third color 11c as deterioration progresses. In the first benchmark section 4a, the color samples are arranged in order of the first color 11a, the second color 11b and the third color 11c from top to bottom according to a time sequence in which deterioration of the biofuel progresses. In the second benchmark section 4b, the color samples are arranged in order of the third color 11c, the second color 11b and the first color 11a from top to bottom so as to be reverse to the order of arrangement of the color samples of the first benchmark section 4a. The color samples 11a, 11b and 11c of the first and second benchmark sections 4a and 4b are located behind the sight glass 3 and, therefore, can be observed through the biofuel introduced into the fuel-display passage 5. Based upon the color samples observed this way, deterioration degrees can be determined.

The color samples 11a, 11b and 11c do not have to be printed and may instead be painted, for example. The background color of the color samples 11a, 11b and 11c is not limited to white and may be a different color.

Storage amount of the biofuel in the fuel tank 1 varies depending on the fuel consumption by the running of the internal combustion engine as well as on the refilling of fresh fuel. In addition, a water layer formed under the biofuel by dew condensation also varies in thickness. These factors cause change of the liquid levels of the biofuel and water layer in the fuel tank 1 and further change of the liquid level in the fuel-display passage 5 of the sight glass 3 in a similar manner.

The biofuel exists in a range of the level height defined by a level lower than the liquid level of the biofuel and a level higher than the liquid level of the water layer. A deterioration degree can be determined in this range by comparing the biofuel with the color samples 11a, 11b and 11c of the benchmark sections 4a and 4b. Considering the foregoing matters, the vertical position of the sight glass 3 is set as stated below.

The water layer in the fuel tank 1 is properly removed by draining. Assuming that the drainage is timely performed with a reasonable care, it is possible to specify to some extent an allowable highest position that the liquid level of the water layer can lower in the fuel tank 1 after the drainage. If the sight glass 3 is placed below the allowable highest position of the liquid level of the water layer, the color samples 11a, 11b and 11c coincide with the water layer, so that a deterioration degree may not be determined. The liquid level of the biofuel in the fuel tank 1 drops as a result of fuel consumption. Accordingly, the higher the position of the sight glass 3 is placed, the more frequently the color samples 11a, 11b and 11c coincide with an air layer located above the biofuel, making the deterioration checking impossible.

Based on the foregoing knowledge, in the present embodiment the sight glass 3 is installed in a lowest possible position and yet in a position above the allowable highest position that the liquid level of the water layer reaches after the proper drainage.

Operation of the biofuel deterioration checking device 2 will be described below.

Figure 6:
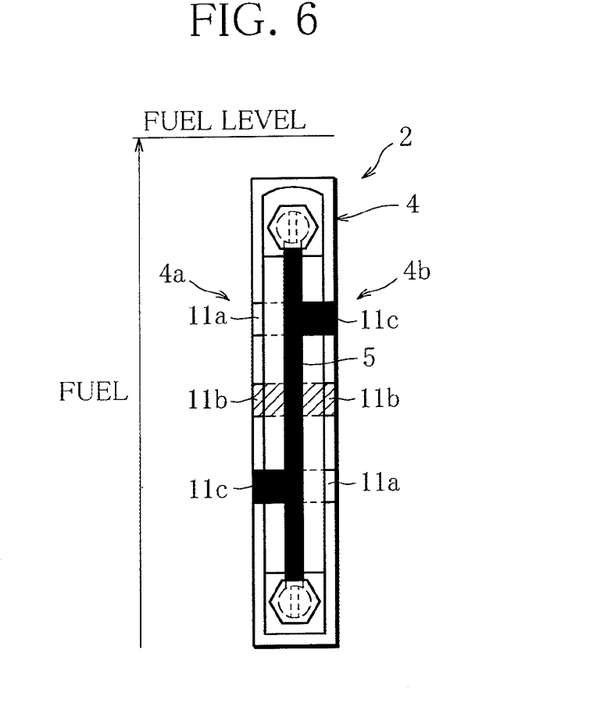
FIG. 6 is an elevation view of the deterioration checking device in a normal state, in which a biofuel is fully introduced into the sight glass.

By the proper installation of the sight glass 3, the liquid level of the biofuel in the fuel tank 1 is higher than the sight glass 3, whereas the liquid level of the water layer is lower than the sight glass 3. As shown in FIG. 6, therefore, the biofuel is introduced into the fuel-display passage 5 of the sight glass 3 from the top through to the bottom end. As explained below, the deterioration checking of the biofuel is made on the basis of the three color samples 11a, 11b and 11c of either one of the first and second benchmark sections 4a and 4b. In the case of FIG. 6, in both the benchmark sections 4a and 4b, all the three color samples 11a, 11b and 11c are observable through the biofuel without being obstructed by the air layer above the biofuel or the water layer under the biofuel. It is then possible to randomly choose either one of the benchmark sections 4a and 4b and use the color samples 11a, 11b and 11c of the chosen benchmark section to determine a deterioration degree of the biofuel.

Figure 7:
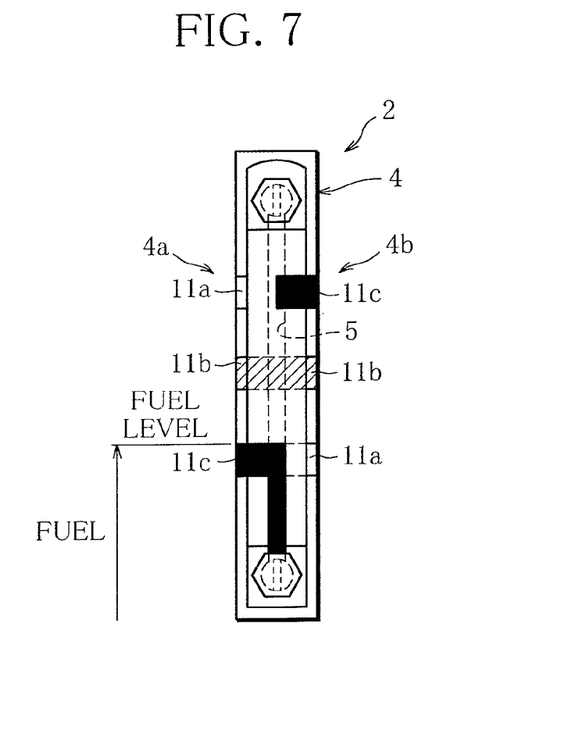
FIG. 7 is an elevation view of the deterioration checking device in a state where a biofuel observable area is limited to a lower part as a result of decrease of a fuel level.
Figure 8:
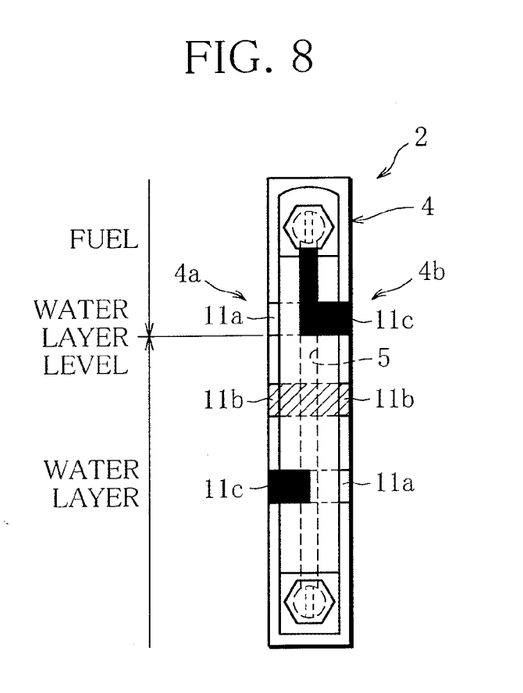
FIG. 8 is an elevation view of the deterioration checking device in a state where the biofuel observable area is limited to an upper part as a result of the rising of a water layer.

The method of the deterioration checking using the deterioration checking device 2 of the present embodiment is based on the phenomenon in which the color sample observable through the biofuel varies among these color samples 11a, 11b and 11c as the deterioration(aging) of the biofuel progresses. In other words, when the biofuel is fresh or almost fresh, only the first color sample 11a is indistinguishably similar to the color of the biofuel and thus is unobservable, whereas the second and third colors 11b and 11c remain observable. When the deterioration of the biofuel progresses, the color of the biofuel becomes similar to the second color 11b and the second color 11b becomes unobservable. If the biofuel reaches a use limit thereof, the color of the biofuel becomes similar to the third color 11c, and the third color 11c becomes unobservable. FIG. 6 shows a state in which the biofuel has reached the use limit, and the color of the biofuel has become indistinguishably similar to the third color 11c. FIGS. 7 and 8 show the same state but at different liquid levels of the biofuel.

In this way, which color sample is observable among the color samples 11a, 11b and 11c depends upon the deterioration(aging) degree of the biofuel. For this reason, for example, after the second color 11b becomes unobservable, it is necessary to pay more attention to the indication of the deterioration checking device 2. When the third color 11c later becomes unobservable thereafter, then it indicates that the biofuel has reached an undesirable limit for use. The biofuel in the tank is then refilled. It is therefore possible to properly determine the deterioration degree of the biofuel, and promptly and timely deal with the deterioration, and thus to prevent various problems caused when deteriorated biofuel is used.

Moreover, the deterioration checking device 2 of the present embodiment has a simple configuration, comprising the sight glass 3 into which the biofuel in the fuel tank 1 is introduced, and the first and second benchmark sections 4a and 4b having the color samples 11a, 11b and 11c. The deterioration checking device 2 does not at all require any sensors and processing circuits as required by the technologies disclosed in the Patent Documents 1 and 2. The deterioration checking device 2 can be utilized with a simple and inexpensive system, and exerts the excellent advantage that the device 2 is unlikely to break down because of the simple configuration thereof, thereby offering high reliability.

As is clear from the foregoing, in the process to determine the use limit of biofuel, the third color 11c corresponding to the use limit is more important than that based upon the first or second color 11a or 11b. Such a simple determination makes it possible to detect the use limit of the biofuel and refill the biofuel with proper timing. If the biofuel is introduced fully into the fuel-display passage 5 of the sight glass 3 as mentioned above, the third color 11c coincides with the biofuel, regardless of whatever vertical position the third color 11c is in. For this reason, there is no problem in determining the use limit.

However, if the biofuel is not properly refilled, the fuel level in the fuel-display passage 5 drops as the liquid level of the biofuel in the fuel tank 1 lowers as shown in FIG. 7, and the observable area of the biofuel is limited to a lower part. In such case, if the third color 11c is located above the fuel level as in the second benchmark section 4b, it is impossible to determine the use limit itself. If the water layer is not properly drained, the liquid level of the water layer in the fuel-display passage 5 rises as the liquid level of the water layer in the fuel tank 1 rises as shown in FIG. 8, and the observable area of the biofuel is limited to an upper part. In such case, if the third color 11c is located under the liquid level of the water layer as in the first benchmark section 4a, it is impossible to determine the use limit itself.

As a measure against such a situation, in this embodiment, the arrangement of the color samples 11a, 11b and 11c of the first benchmark section 4a and that of the color samples 11a, 11b and 11c of the second benchmark section 4b are reversed.

In this way, even if the fuel level in the fuel-display passage 5 drops due to absence of fuel refilling, the use limit of the biofuel can be determined by observing the third color 11c through the biofuel as long as the liquid level of the biofuel is above the third color 11c of the first benchmark section 4a. Furthermore, even if the liquid level of the water layer in the fuel-display passage 5 rises due to absence of draining, the use limit of the biofuel can be determined by observing the third color 11c through the biofuel as long as the liquid level of the water layer is below the third color 11c of the second benchmark section 4b.

According to the present embodiment, compared with a case in which a single benchmark section (for example, either one of the first and second benchmark sections 4a and 4b) is provided, the deterioration degree of the biofuel can be determined on more occasions, regardless of variations of the liquid levels of the biofuel and water layer in the fuel tank 1. In particular, since the important use limit of the biofuel can be determined, the biofuel can be exchanged with more proper timing.

Moreover, the sight glass 3 is placed above the allowable highest position of the liquid level of the water layer in the fuel tank 1. This means that drainage is required when the water layer is observed in the fuel-display passage 5. The sight glass 3 of the deterioration checking device 2 can therefore be used to learn proper the timing for drainage. Thus it is also possible to provide the advantage that the sight glass 3 enables proper drainage.

The present embodiment employs the method in which the color samples 11a, 11b and 11c of the first and second benchmark sections 4a and 4b are located behind the sight glass 3, and the deterioration degree of the biofuel is determined by observing the color samples 11a, 11b and 11c through the biofuel in the fuel-display passage 5.

The method is, however, not limited to this. For example, the color samples 11a, 11b and 11c of the first and second benchmark sections 4a and 4b may be placed adjacent to the fuel-display passage 5 so that the color shade(hue and tone) of the biofuel in the fuel-display passage 5 may be compared to the colors (shades) of the color samples 11a, 11b and 11c.

In the foregoing embodiment, as shown in FIG. 2, for example, the color samples 11a, 11b and 11c of the benchmark sections 4a and 4b extend to the right and left beyond the sight glass 3 so that the color samples can be seen from the front. If the back face (color sample side) of the sight glass 3 is colored all in white so that the original color of the biofuel may be observed from the front outside, the color samples 11a, 11b and 11c of the benchmark sections 4a and 4b may be placed on the right and left sides of the biofuel in the fuel-display passage 5. In this case, the same color as the biofuel is chosen from the three color samples 11a, 11b and 11c to determine the deterioration degree of the biofuel. In such a case, the same operation and advantages as those of the embodiment can be provided, and therefore, overlapping descriptions will be omitted.

Figure 9:
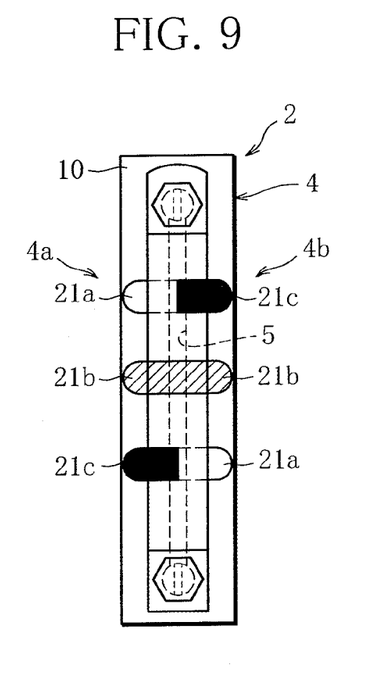
FIG. 9 is an elevation view of a deterioration checking device of another embodiment of the present invention, in which capsules filled with deteriorated biofuels are used as color samples.
Figure 10:
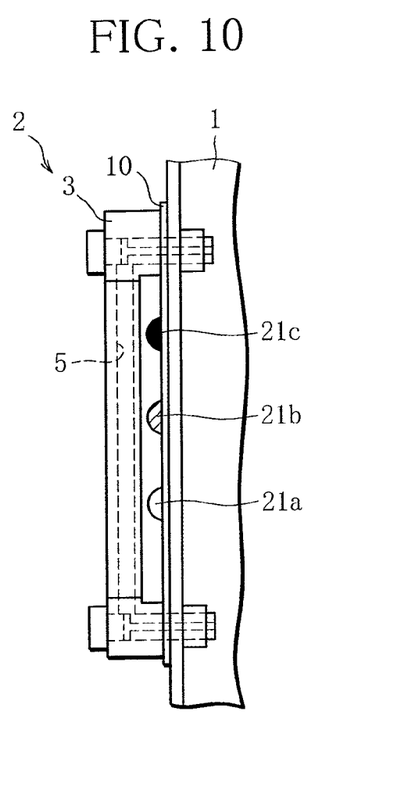
FIG. 10 is a sectional view of the deterioration checking device of the embodiment shown in FIG. 9

In the above embodiment, the color samples 11a, 11b and 11c are printed or painted on the base plate 10. Alternatively, it is also possible to utilize, as color samples, transparent capsules 21a, 21b and 21c filled with different biofuels which have different degrees of the deterioration, as shown in FIGS. 9 and 10. The transparent capsules 21a, 21b and 21c are arranged in upper, middle and lower positions of the base plate 10, respectively. The transparent capsules 21a, 21b and 21c are each divided into right and left portions in the inside at the center. The deteriorated biofuels corresponding to the first, second and third colors 11a, 11b and 11c, in order from above, are filled in the left halves of the respective transparent capsules 21a, 21b and 21c. Likewise, the deteriorated biofuels corresponding to the third, second and first colors 11c, 11b and 11a, in order from above, are filled in the right halves of the respective capsules 21a, 21b and 21c.

In this way, as in the foregoing embodiment, deterioration degree can be determined by observing the deteriorated biofuels in the transparent capsules 21a, 21b and 21c through the biofuel in the fuel-display passage 5. Moreover, if the back face of the sight glass 3 is colored in white and the deteriorated biofuels in the transparent capsules 21a, 21b and 21c are located adjacent to and on the right and left sides of the biofuel in the fuel-display passage 5, the degree of deterioration can be determined by comparing these colors. It is therefore possible to not only obtain the same operation and advantages as those of the foregoing embodiment but also achieve further accurate deterioration determination if the actually deteriorated biofuels are used as the color samples.

The descriptions of the embodiments will be finished here, but the invention is not limited to the aforementioned embodiments. For example, in the above embodiments, the invention is embodied in the form of the deterioration checking device 2 and the liquid storage tank 1 provided with the device for biofuels, lubrication oils, and hydraulic oils, which is utilized by the hydraulic excavator. However, the liquid to be subjected to the deterioration checking is not limited to the above-mentioned fuels and oils. For example, if light oil is used as a fuel for the internal combustion engine, the invention may be embodied in the form of a deterioration checking device intended to determine a deterioration degree of the light oil.

The configurations of the sight glass 3 and the benchmark sections 4a and 4b are also not limited to those described in the embodiments. For example, the sight glass 3 may be altered in shape, and the number of the color samples 11a, 11b, 11c, 21a, 21b and 21c may be increased or decreased.

EXPLANATION OF REFERENCE MARKS

1: fuel tank (liquid storage tank)
2: liquid quality checking device (deterioration checking device)
3: sight glass (observation window)
4a: first benchmark section
4b: second benchmark section
11a, 11b, 11c: color sample
21a, 21b, 21c: transparent capsule (color sample)

The invention claimed is:

1. A liquid quality checking device comprising:
an observation window that is attachable onto a liquid storage tank and extends in a vertical direction along which a liquid level of a liquid stored in the liquid storage tank changes, the observation window permitting a change in quality of the liquid to be observed as a change in color of the liquid; and
first and second benchmark sections that are placed close to the observation window, each of said first and second benchmark sections having a plurality of color samples, corresponding to a plurality of different quality degrees of the liquid, arranged along the observation window; wherein
in the first benchmark section, the color samples are arranged along the observation window in order of specific stages through which deterioration of the liquid quality progresses, and
in the second benchmark section, the color samples are arranged along the observation window in order reverse to the order of the color samples of the first benchmark section.

2. The liquid quality checking device according to claim 1, wherein the plurality of color samples are formed by filling transparent capsules with liquids at the plurality of different quality degrees.

3. A liquid storage tank provided with the liquid quality checking device according to claim 2.

4. The liquid storage tank according to claim 3, wherein a vertical position of the liquid quality checking device is set so that a lower end of the observation window is located above an allowable highest position that a liquid level of a contaminant forming a layer under the liquid in the liquid storage tank can lower.

5. A liquid storage tank provided with the liquid quality checking device according to claim 1.

6. The liquid storage tank according to claim 5, wherein a vertical position of the liquid quality checking device is set so that a lower end of the observation window is located above an allowable highest position that a liquid level of a contaminant forming a layer under the liquid in the liquid storage tank can lower.

* * * * *